United States Patent
Lyons et al.

(10) Patent No.: US 8,424,534 B2
(45) Date of Patent: Apr. 23, 2013

(54) LOADING DILATOR WITH TRANSITION BALLOON

(75) Inventors: Drew P. Lyons, Ellettsville, IN (US); Andrew K. Hoffa, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1072 days.

(21) Appl. No.: 11/799,135

(22) Filed: May 1, 2007

(65) Prior Publication Data

US 2008/0275391 A1    Nov. 6, 2008

(51) Int. Cl.
*A61M 29/00* (2006.01)
*A61M 16/00* (2006.01)

(52) U.S. Cl.
USPC ............... 128/898; 128/207.14; 604/103.08; 604/104; 606/196

(58) Field of Classification Search ............ 128/207.29; 604/103.08, 104; 606/196
See application file for complete search history.

(56) References Cited

U.S. PATENT DOCUMENTS

| | | | |
|---|---|---|---|
| 3,087,493 A | 4/1963 | Schossow | |
| 4,248,236 A | 2/1981 | Linder | 128/349 |
| 4,364,391 A * | 12/1982 | Toye | 128/207.29 |
| 4,889,112 A | 12/1989 | Schachner et al. | 128/200.26 |
| 4,913,139 A | 4/1990 | Ballew | 128/200.11 |
| 5,058,580 A | 10/1991 | Hazard | 128/207.15 |
| 5,217,005 A | 6/1993 | Weinstein | 128/200.26 |
| 5,217,007 A | 6/1993 | Ciaglia | 128/207.29 |
| 5,507,279 A | 4/1996 | Fortune et al. | 128/200.26 |
| 5,515,844 A | 5/1996 | Christopher | 128/200.26 |
| 5,653,230 A | 8/1997 | Ciaglia et al. | 128/207.15 |
| 5,690,669 A | 11/1997 | Sauer et al. | 606/196 |
| 5,749,357 A | 5/1998 | Linder | 128/200.26 |
| 5,803,080 A * | 9/1998 | Freitag | 128/207.14 |
| 5,967,143 A | 10/1999 | Klappenberger | 128/207.29 |
| 6,109,264 A * | 8/2000 | Sauer | 128/207.29 |
| 6,286,509 B1 * | 9/2001 | Nash et al. | 128/207.14 |
| 6,298,851 B1 | 10/2001 | Parota et al. | 128/207.29 |
| 6,382,209 B1 | 5/2002 | Toye | 128/207.14 |
| 6,637,435 B2 | 10/2003 | Ciaglia et al. | 128/207.29 |
| 6,662,804 B2 * | 12/2003 | Ortiz | 128/207.14 |
| 6,706,017 B1 | 3/2004 | Dulguerov | 604/164.01 |
| 6,742,519 B2 | 6/2004 | Turnbull | 128/207.29 |

(Continued)

FOREIGN PATENT DOCUMENTS

EP   0 294 200 A2   12/1988
EP   0 784 989 A2   7/1997

(Continued)

*Primary Examiner* — Kathleen Holwerda
*Assistant Examiner* — Sarah W Aleman
(74) *Attorney, Agent, or Firm* — Brinks Hofer Gilson & Lione

(57) ABSTRACT

A loading dilator for positioning a medical apparatus across a stoma formed in a body wall of a patient. The medical apparatus, such as a tracheotomy tube, is sized to fit over a portion of the loading dilator during positioning of the apparatus across the stoma. The loading dilator includes an elongated dilator body having a tapered distal end for facilitating entry into the stoma. The dilator body has an inflatable balloon disposed along an outer surface at the distal end. The balloon is inflatable to a configuration such that a generally smooth diametrical transition is formed between the elongated dilator body and a leading end of the medical apparatus when the medical apparatus is fit over the loading dilator.

5 Claims, 4 Drawing Sheets

U.S. PATENT DOCUMENTS

| | | | |
|---|---|---|---|
| 7,036,510 B2 | 5/2006 | Zgoda et al. | 128/207.29 |
| 2004/0181273 A1* | 9/2004 | Brasington et al. | 623/1.15 |
| 2005/0183729 A1* | 8/2005 | Fischer, Jr. | 128/207.29 |
| 2006/0081260 A1 | 4/2006 | Eells et al. | 128/207.29 |
| 2006/0090761 A1 | 5/2006 | Kurrus | 128/207.15 |
| 2006/0124134 A1* | 6/2006 | Wood | 128/207.29 |

FOREIGN PATENT DOCUMENTS

| | | |
|---|---|---|
| GB | 708477 | 5/1954 |
| GB | 2 084 023 A | 4/1982 |
| WO | WO 97/38749 | 10/1997 |

* cited by examiner

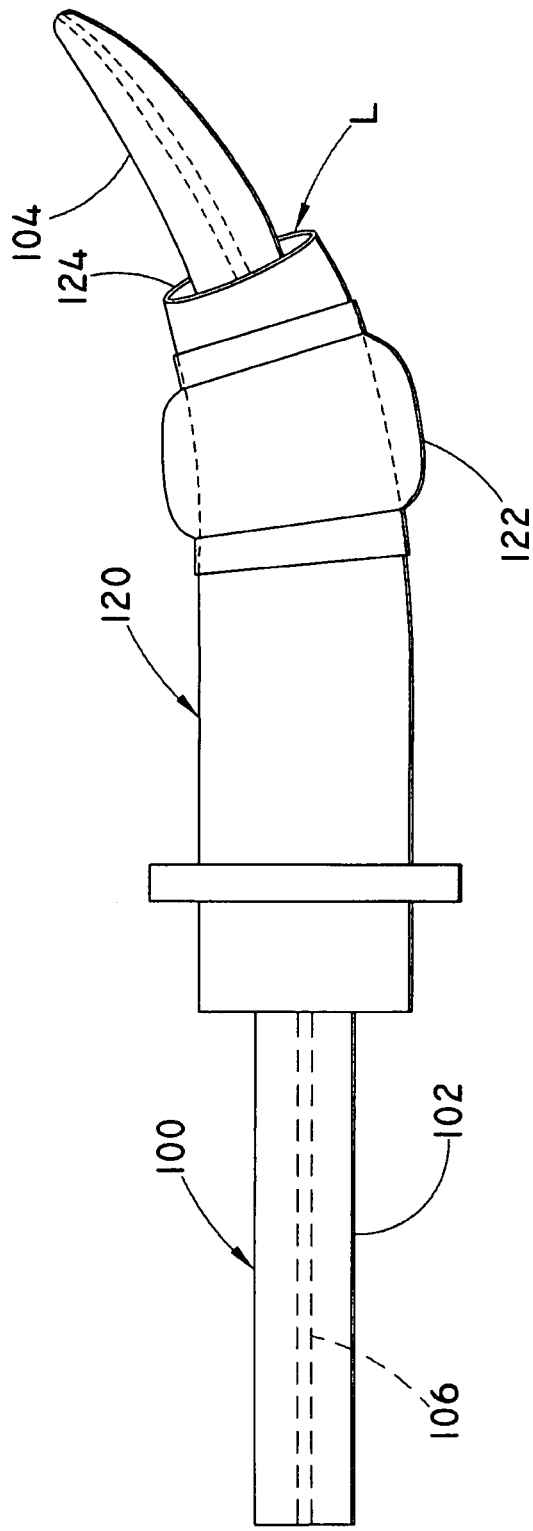

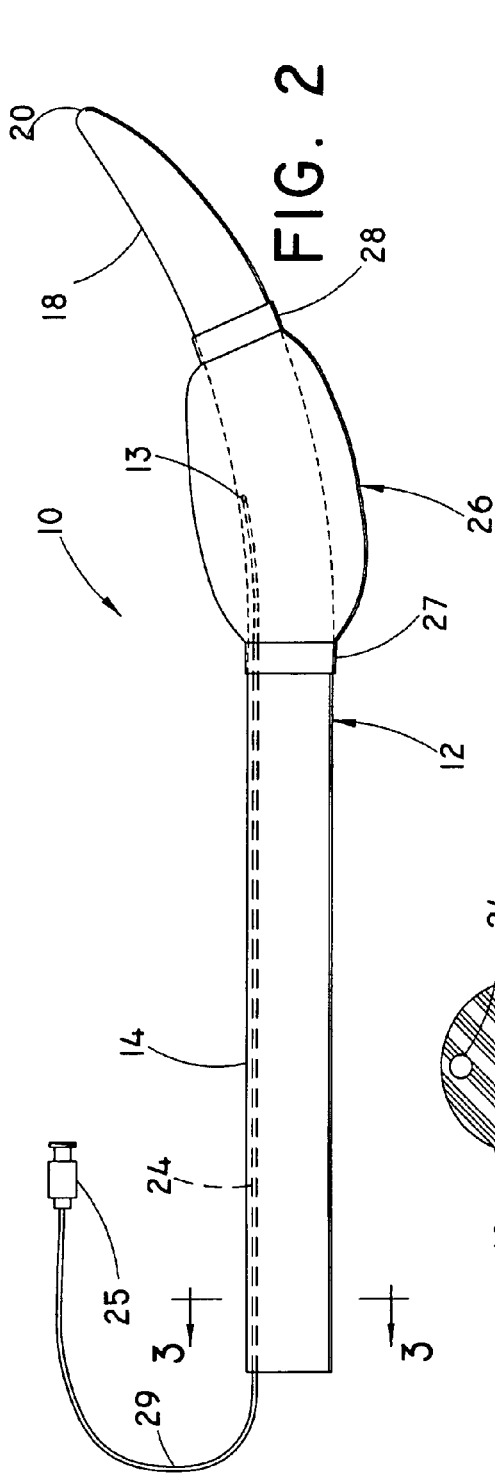
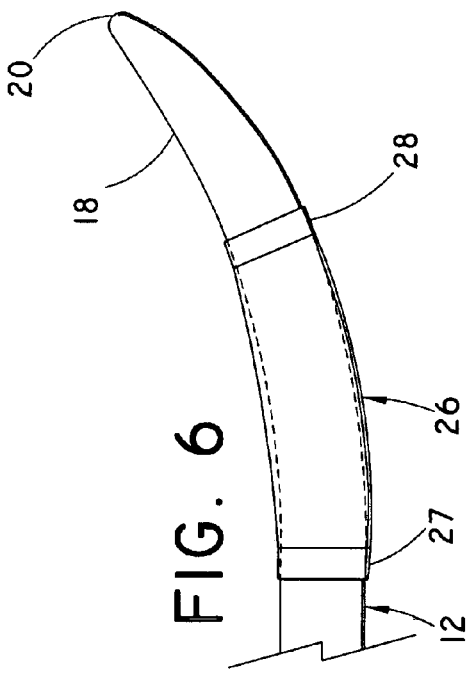

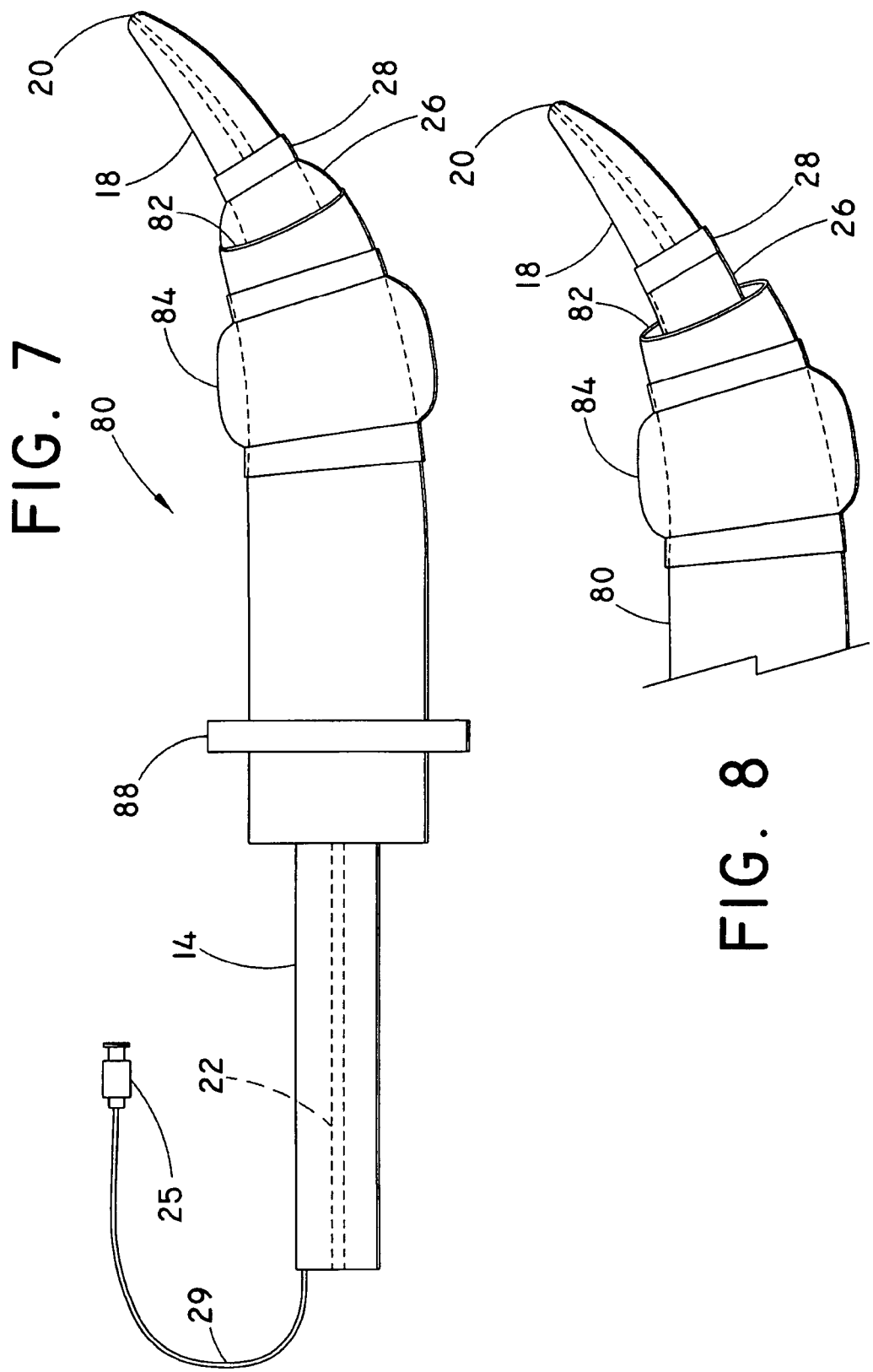

LOADING DILATOR WITH TRANSITION BALLOON

BACKGROUND

1. Technical Field

This application relates to a dilator for dilating an opening in the body of a patient for a medical use. More particularly, the invention relates to a loading dilator having a transition balloon at a distal end thereof for use in placement of a medical device, such as a tracheostomy tube, across the body opening.

2. Background Information

The creation of an adequate air passageway is a critical step in maintaining the ability of a seriously ill or injured patient to breathe, or in performing resuscitation on a patient unable to breathe. Endotracheal intubation (the placement of a tube through the nostrils or mouth and into the trachea itself) is a widely-used method for establishing an air passageway. However, in order to establish an optimal air passageway for endotracheal intubation, the trachea, nostrils and/or mouth must normally be free, or at least substantially free, of obstruction. When an obstruction is present, endotracheal intubation is not generally possible, and an alternative passageway for airflow must be established.

The most direct way to provide an air passageway under these circumstances is to form a stoma, or opening, in the tracheal wall. Once formed, a tracheostomy tube is inserted through the stoma. Conventional tracheostomy tubes often include an open distal aperture and a circumferential inflatable cuff. The cuff provides a seal between the tracheal wall and the tracheostomy tube at a location proximal to the distal aperture. The seal prevents the intrusion of blood, tissue or foreign matter into the lower trachea, bronchi and lungs, while permitting complete control and monitoring of the airflow established through the tracheostomy tube, including the provision of positive pressure ventilation. The open distal aperture provides a passageway for air into the lungs of the patient.

Several methods and devices are known for forming, or enlarging, a stoma in a tracheal wall. In one such method, a small opening is initially made in the tracheal wall. A needle is inserted through the small opening, such that the tip of the needle is in the interior space of the trachea. A wire guide is then passed into the trachea through a bore in the needle, and the needle is thereafter withdrawn. Sequentially sized dilators are then advanced over the wire guide to facilitate gradual dilation of the tracheal entrance to an appropriate size.

Recently, a single curved dilator, sold by Cook Incorporated of Bloomington, Ind., under the name BLUE RHINO®, has been developed that avoids the necessity of utilizing multiple dilators. The BLUE RHINO® dilator, so called because its shape resembles the horn of a rhinoceros, has a distal end portion that is curved in a substantially continuous manner, wherein an increasingly larger diameter portion of the dilator may be inserted into the trachea, thereby facilitating clearance of the posterior tracheal wall. Further description of the BLUE RHINO® dilator is provided in U.S. Pat. No. 6,637,435, incorporated by reference herein.

Another method for forming or enlarging a stoma in a tracheal wall for introduction of a tracheostomy tube is described in U.S. Pat. No. 5,653,230, incorporated by reference herein. This method employs a balloon catheter having an inflatable balloon at a distal end of the catheter. The catheter is inserted over a percutaneously inserted wire guide, and the catheter is advanced along the wire guide until the balloon lies across the tracheal wall. The balloon is then inflated to radially dilate a portion of the tracheal wall, thereby forming a stoma in the wall that corresponds to the inflated diameter of the balloon.

Following formation of the stoma by any of the known methods, an introducer/loading dilator is pre-loaded with a tracheostomy tube, and the distal end of the apparatus is passed through the stoma over the previously-inserted wire guide. It is desirable to provide a dilator/tracheostomy tube combination that has a generally smooth transition from dilator to tube, thereby facilitating entry of the distal, or leading, end portion of the tube through the stoma. However, since there are a number of different sizes and manufacturers of tracheostomy tubes, there is a possibility that a significantly-sized lip (resulting from the respective differences in diameter between the loading dilator and the leading end of the tracheostomy tube), may be present at the transition between the loading dilator and the distal end of the tracheostomy tube. One example of a lip L is illustrated in FIG. 1. The presence of a lip at a junction between a smaller diameter loading dilator and a larger diameter tracheostomy tube can hinder insertion of the tracheostomy tube through the stoma, and can increase the trauma experienced by the patient upon insertion of the tube.

It would be desirable to provide a loading dilator that is sized to accommodate tracheostomy tubes having a range of diameters, and that is structured to minimize the transition between the loading dilator and the tracheostomy tube upon insertion of a dilator/tracheostomy tube apparatus.

BRIEF SUMMARY

The problems of the prior art are addressed by the features of the present invention. In one form thereof, the invention comprises a loading dilator for positioning a medical apparatus across a stoma formed in a body wall of a patient, the medical apparatus being sized to fit over a portion of the loading dilator during positioning of the apparatus across the stoma. The loading dilator comprises an elongated dilator body having a proximal end and a distal end, wherein at least a portion of the distal end is tapered for facilitating entry into the stoma. The dilator body has an inflatable balloon disposed along an outer surface at the distal end, the balloon being inflatable to a configuration such that a generally smooth diametrical transition is formed between the elongated dilator body and a leading end of the medical apparatus when the medical apparatus is fit over the loading dilator.

In another form thereof, the invention comprises an assembly for establishing a ventilation passageway in the tracheal wall of a patient. The assembly comprises a loading dilator and a tracheostomy tube carried on an outer surface of the loading dilator. The loading dilator comprises an elongated dilator body having a proximal end and a distal end, at least a portion of the distal end being tapered for facilitating entry into a stoma in the tracheal wall. The dilator body has an inflatable balloon disposed along an outer surface of the distal end, the balloon being inflatable to a diameter such that a generally smooth diametrical transition is formed between the elongated dilator body and a leading end of the tracheostomy tube when the tracheostomy tube is carried on the dilator.

In yet another form thereof, the invention comprises a method for positioning a medical apparatus across a stoma formed in a body wall of a patient. A loading dilator is provided for carrying the medical apparatus. The loading dilator comprises an elongated dilator body having a distal end, wherein at least a distal tip portion of the distal end is tapered for facilitating entry into the stoma. The dilator body has an inflatable balloon disposed along an outer surface of the distal end, wherein the balloon is inflatable to a diameter such that a generally smooth diametrical transition may be formed between the elongated dilator body and a leading end of the medical apparatus when the medical apparatus is fit over the loading dilator. The medical apparatus is loaded onto the loading dilator, and positioned thereon such that a portion of the balloon distal end extends distally beyond a leading end of the medical apparatus. The balloon is inflated such that the extending balloon distal end portion provides a generally smooth diametrical transition between an outer diameter of the loading dilator and the medical apparatus leading end. The distal end of the elongated dilator body is inserted into the stoma, and the loading dilator and medical apparatus are advanced such that a portion of the medical apparatus lies across the stoma.

BRIEF DESCRIPTION OF THE DRAWINGS

FIG. 1 is a side view of a prior art loading dilator, wherein a tracheostomy tube is loaded on the dilator;

FIG. 2 is a side view of a loading dilator according to one embodiment of the present invention, illustrating the transition balloon in an inflated condition;

FIG. 3 is a sectional view of the dilator taken through lines 3-3 of FIG. 2;

FIG. 4 is a sectional view of the dilator showing an alternate placement of the inflation lumen;

FIG. 5 is a sectional view of an alternate embodiment of the dilator having a channel for receiving the inflation lumen;

FIG. 6 is a side view of the loading dilator shown in FIG. 2, with the transition balloon in an uninflated condition;

FIG. 7 is a side view of the loading dilator of FIG. 2, showing a tracheostomy tube loaded on the loading dilator, with the transition balloon in an inflated condition;

FIG. 8 is a side view of a portion of the loading dilator and tracheostomy tube as shown in FIG. 7, with the transition balloon in an uninflated condition.

DETAILED DESCRIPTION OF THE DRAWINGS AND THE PRESENTLY PREFERRED EMBODIMENTS

Figure 9:
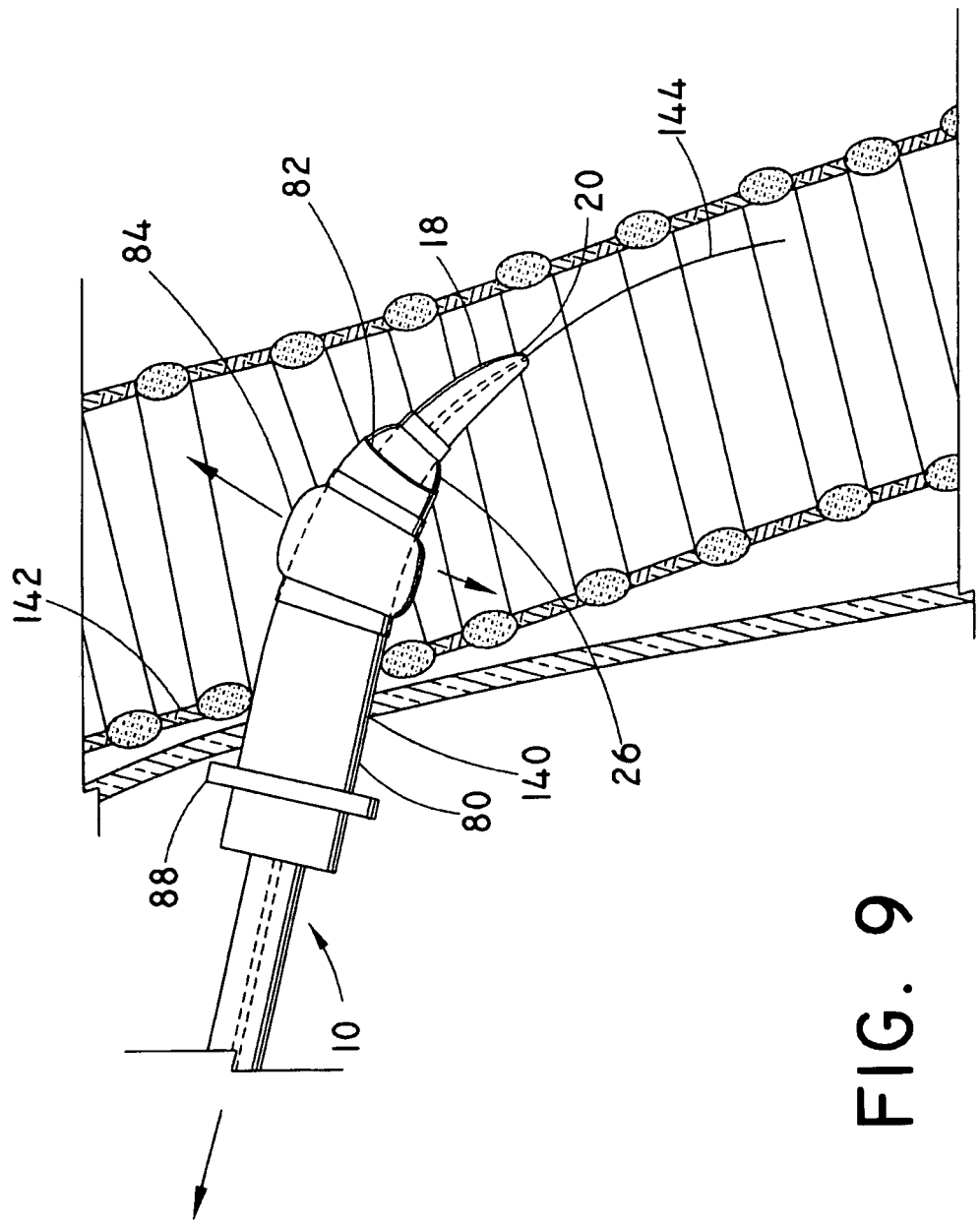
FIG. 9 is a view illustrating the use of the loading dilator in the placement of a tracheostomy tube across a stoma in the tracheal wall.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" are used to describe the axial ends of the loading dilator of the present invention, as well as the axial ends of various component features. The "proximal" end is used in conventional manner to refer to the end of the dilator (or component) that is closest to the operator during use of the loading dilator. The "distal" end is used in conventional manner to refer to the end of the dilator (or component) that is initially inserted into the patient, or that is closest to the patient.

FIG. 1 illustrates a side view of a prior art loading dilator 100. In the figure shown, a tracheostomy tube 120 having an inflatable cuff 122 and a distal end 124 is loaded onto the outer surface of the loading dilator for placement across the tracheal wall of a patient.

Prior art loading dilator 100 includes an elongated body 102 having a distal end 104 that is tapered for ease of entry into the dilated hole previously formed in the tracheal wall. A lumen 106 (shown in phantom) extends through loading dilator 100 for passage of a wire guide (not shown) therethrough. Typically, elongated dilator body 102 is gently curved at the distal end portion to ease entry of the tracheostomy tube through the tracheal wall, and to generally conform to the anatomy within the cavity of the trachea.

In order to accommodate patients of varying sizes, loading dilators and tracheostomy tubes are provided in a variety of different diameters. Ideally, the respective diameters of the loading dilator and the tracheostomy tube will be substantially matched, such that there is only a minimal diametrical transition between the loading dilator and the distal end of the tracheostomy tube. As a result, the trauma experienced by the patient upon insertion of the tracheostomy tube through the tracheal wall will be minimized. However, due to the wide variance in diameters between the loading dilators and tracheostomy tubes that may be available to the physician in the operating room at any one time, it may not be possible to closely match the diameters of the respective dilators and/or tracheostomy tubes available to the physician. In some cases, selection of an available loading dilator and tracheostomy tube may result in the presence of a lip, or a significant diametrical difference between the loading dilator and the distal end of the tracheostomy tube at the transition.

A loading dilator/tracheostomy tube combination having a lip "L" is shown in the prior art combination of FIG. 1. The lip L shown in FIG. 1 is somewhat exaggerated from that which may typically be expected, and is shown in the figure to aid in identifying the position of the transition referenced herein. The presence of a lip of any size at the transition of the dilator 100 and the distal end 124 of the tracheostomy tube 120 will cause at least some trauma to the patient upon introduction of the tracheostomy tube through the tracheal wall, and the presence of a larger lip may cause significant additional trauma to the patient.

FIG. 2 is a side view of a loading dilator 10 according to an embodiment of the present invention. Loading dilator 10 includes an elongated body 12 having a proximal end 14 and a distal end 18. At least a portion of distal end 18 tapers to a distal tip 20. Similar to prior art dilator body 102 of FIG. 1, dilator body 12 is preferably provided with a gentle curve at the distal end portion of the dilator body. Dilator body 12 may be formed from any medical grade, synthetic materials known in the art for such use.

A transition balloon 26 is provided at the distal end portion of the loading dilator. Preferably, the balloon is positioned along the gently curved surface of dilator body 12. Transition balloon 26 is preferably a semi-compliant or non-compliant balloon formed from a medical grade composition well known for such purpose, such as PET or other flexible but generally inelastic material. Balloon 26 is provided with proximal 27 and distal 28 end portions for adhering or otherwise bonding with the outer surface of dilator body 12. Preferably, balloon ends 27, 28 are glued or heat bonded to dilator body 12 in well-known fashion. The transition balloon 26 of loading dilator 10 is shown in FIG. 2 in an inflated condition. FIG. 6 illustrates the distal portion of loading dilator 10 with balloon 26 in an uninflated condition.

In a preferred embodiment, dilator body 12 has at least two lumens extending at least partially therethrough. As shown in the sectional view of FIG. 3, a first lumen 22 extends longitudinally through the center of dilator body 12 and is sized to permit passage of a wire guide therethrough in conventional fashion. A second lumen 24 comprises an inflation lumen for transmission of an inflation fluid, such as air or saline, from a fluid source (not shown), to the interior space of balloon 26. Dilator body 12 includes an exit port 13 that communicates with the interior space of the balloon in well known fashion for transmission of the inflation fluid from lumen 24. As shown in the embodiment of FIG. 2, loading dilator 10 may also include an inflation hub 25 configured for engagement with a corresponding hub on the fluid source, and an extension tube 29 for transmission of the inflation fluid to inflation lumen 24.

FIG. 4 illustrates a sectional view of an alternative embodiment of dilator 10. In this embodiment, inflation lumen 24A does not extend through the interior of dilator body 12. Rather, a tubular member 31 extends longitudinally along the outer surface of dilator body 12, and terminates within the interior space of balloon 26. Inflation lumen 24A extends through the interior of tubular member 31. Preferably, tubular member 31 is glued or otherwise adhered to the outer surface of dilator body 12.

FIG. 5 illustrates a further alternative wherein dilator body 12 is provided with a shallow longitudinal channel 19 along its outer surface. In this embodiment, tubular member 31 can track the channel from the source for the inflation fluid to the interior of the balloon. Inflation lumen 24B extends through tubular member and communicates with the interior space of the balloon, in the same manner as the embodiment of FIG. 4.

FIG. 7 illustrates loading dilator 10 having a conventional tracheostomy tube 80 loaded on the outer surface of dilator body 12 in well known fashion. Tracheostomy tube 80 has an open distal, or leading, end 82 and a circumferential inflatable cuff 84 positioned near open distal end 82. The inflatable cuff provides a seal between the tracheal wall and the tracheostomy tube to prevent the intrusion of blood, tissue and other foreign matter into the lower trachea, bronchi and lungs. The open distal end 82 provides a passageway for air into the lungs of the patient. A conventional flange 88 may be provided at the proximal end of the tracheostomy tube for abutment against the skin of the patient when tracheostomy tube 80 is inserted through the stoma. Tracheostomy tubes are well known in the art, and tracheostomy tube 80 as shown herein is merely one example of a suitable tracheostomy tube that can be utilized in connection with the inventive loading dilator.

Transition balloon 26 is shown in FIG. 7 in an inflated condition. In contrast, FIG. 8 illustrates a portion of a loading dilator/tracheostomy tube combination wherein the balloon 26 is in an uninflated condition. As shown in FIG. 8, when balloon 26 is uninflated, a significant lip may be present at the transition between the dilator body and tracheostomy tube distal end 82. The presence of the lip may cause difficulty in inserting the tracheostomy tube through the stoma, thereby resulting in additional trauma to the patient.

When transition balloon 26 is inflated as shown in FIG. 7, a substantially non-traumatic diametrical transition is created between loading dilator 10 and distal end 82 of tracheostomy tube 80. This may be observed by viewing the gradual transition along the surface of balloon 26 between loading dilator distal end 18 and tracheostomy tube distal end 82. For ease of entry into the stoma, it is preferred to provide a balloon 26 having a gently tapered distal end portion upon inflation, as shown in FIG. 7. However, although a smooth taper is preferred, the taper need not necessarily be a substantially smooth one as shown. Since the balloon has a greater amount of flexibility, or "give", when compared to the tracheostomy tube, even a non-tapered, or a less smooth taper, will provide some benefits upon insertion through the tracheal wall.

Preferably, transition balloon 26 will be formed to have a curve, such that it conforms to the curve found in most conventional tracheostomy tubes. However, this is not a critical factor, and if desired, a straight balloon can be provided.

Operation of the loading dilator 10 will now be described in connection with its preferred use, namely, positioning a tracheostomy tube in a stoma 140 formed in the tracheal wall 142 of a patient. This is illustrated in FIG. 9. Initially, a wire guide 144 is percutaneously inserted through the tracheal wall in well-known fashion, such as through the interior of a previously-inserted hollow needle (not shown). Following removal of the needle, the wire guide to remains in place across the tracheal wall. The opening is then dilated using, e.g., a dilator such as the curved BLUE RHINO® dilator described in the incorporated by reference U.S. Pat. No. 6,637,435, or the balloon dilator as described in the incorporated by reference U.S. Pat. No. 5,653,230.

The tracheostomy tube 80 is then loaded onto the outer surface of loading dilator 10 such that a distal end portion of transition balloon 26 extends distally beyond leading end 82 of tracheostomy tube 80. The transition balloon is then inflated until a generally smooth transition is established from leading tracheostomy tube end 82 to distal end 18 of the loading dilator. This is best shown in FIG. 7. The loading dilator/tracheostomy tube combination is then manually advanced and inserted through the stoma 140 to the desired placement, and the tracheostomy tube cuff 84 may then be inflated to position the tracheostomy tube within the trachea. Once the insertion is complete and the tracheostomy tube has been properly positioned, transition balloon 26 is deflated. The loading dilator 10 is then withdrawn. Further details relating to a tracheostomy tube insertion procedure not specific to the features of the present invention are discussed in the incorporated by reference patents.

An advantage of the loading dilator of the present invention is that the physician has considerable discretion with regard to the degree of inflation of the balloon. Thus, the physician can continue to add inflation fluid (e.g., air or saline solution) until a satisfactory transition "look and feel" is achieved. Providing a loading dilator having a balloon that is capable of inflation to a variety of diameters significantly increases the versatility of the loading dilator by allowing it to be used with tracheostomy tubes of many different diameters.

It is therefore intended that the foregoing detailed description be regarded as illustrative rather than limiting, and that it be understood that it is the following claims, including all equivalents, that are intended to define the spirit and scope of this invention.

What is claimed is:

1. A method for positioning a tracheostomy tube across a stoma formed in the tracheal wall of a patient, comprising:

providing a loading dilator for carrying the tracheostomy tube, the loading dilator comprising an elongated dilator body having a distal end, a distal tip of said distal end being tapered for facilitating entry into said stoma, said dilator body having a curve along a distal portion thereof and having an inflatable balloon disposed along said curved distal portion, said inflatable balloon having a proximal end and a distal end, and being inflatable to a diameter such that a distal taper may be formed between the elongated dilator body and a leading end of the tracheostomy tube when the tracheostomy tube is fit over the loading dilator;

loading the tracheostomy tube onto the loading dilator, and positioning the tracheostomy tube thereon such that a portion of the balloon distal end extends distally beyond a leading end of the tracheostomy tube;

inflating the balloon such that the extending balloon distal end portion provides a distally-directed taper between an outer diameter of the loading dilator and the tracheostomy tube leading end;

inserting the distal end of the elongated dilator body across the stoma formed in the tracheal wall; and axially advancing the loading dilator and tracheostomy tube leading end through the stoma, with the balloon in the inflated condition, such that a portion of the tracheostomy tube lies across the stoma.

2. The method of claim 1, further comprising the step of deflating the balloon, and removing the loading dilator from the tracheostomy tube.

3. The method of claim 2, wherein the balloon is inflatable to a diameter such that a generally smooth transition is formed between the elongated dilator body and the leading end of the tracheostomy tube.

4. The method of claim 3, wherein said elongated dilator body has at least one lumen extending therethrough, said balloon comprising a non-compliant or a semi-compliant balloon composition.

5. The method of claim 1, wherein the tracheostomy tube has a curved portion, and wherein said axially advancing step includes advancing said tracheostomy tube curved portion across said stoma.

* * * * *